US012758100B2

(12) United States Patent
Chen et al.

(10) Patent No.: US 12,758,100 B2
(45) Date of Patent: Oct. 13, 2026

(54) WEARABLE DEVICE AND METHOD FOR PERFORMING REGISTRATION PROCESS IN THE WEARABLE DEVICE

(71) Applicant: PIXART IMAGING INC., Hsin-Chu (TW)

(72) Inventors: Chun-Chih Chen, Hsin-Chu (TW); Yung-Chang Lin, Hsin-Chu (TW); Ming-Hsuan Ku, Hsin-Chu (TW)

(73) Assignee: PIXART IMAGING INC., Hsin-Chu (TW)

( * ) Notice: Subject to any disclaimer, the term of this patent is extended or adjusted under 35 U.S.C. 154(b) by 88 days.

(21) Appl. No.: 18/517,873

(22) Filed: Nov. 22, 2023

(65) Prior Publication Data

US 2024/0081649 A1 Mar. 14, 2024

Related U.S. Application Data

(63) Continuation of application No. 17/030,546, filed on Sep. 24, 2020, now Pat. No. 11,864,864.

(51) Int. Cl.
*A61B 5/00* (2006.01)

(52) U.S. Cl.
CPC .......... *A61B 5/0064* (2013.01); *A61B 5/0082* (2013.01); *A61B 5/681* (2013.01); *A61B 5/6844* (2013.01); *A61B 2560/0266* (2013.01)

(58) Field of Classification Search
CPC ....... G06F 21/32; A61B 5/681; A61B 5/6844; A61B 5/6886; A61B 5/0245; A61B 5/0059; A61B 5/02438; A61B 5/6824; A61B 5/6813; A61B 2562/0238; A61B 2562/043; A61B 2562/046; A61B 2562/063; A61B 2562/066; A61B 2562/146
See application file for complete search history.

(56) References Cited

U.S. PATENT DOCUMENTS

2014/0275852 A1* 9/2014 Hong .................. A61B 5/0002 600/479
2015/0371028 A1 12/2015 Patel
2016/0154952 A1* 6/2016 Venkatraman ... G06Q 20/40145 726/19
2017/0035353 A1* 2/2017 Wu ...................... A61B 5/7235

FOREIGN PATENT DOCUMENTS

CN 105266780 A 1/2016
CN 108242129 A 7/2018
CN 109152542 A 1/2019

* cited by examiner

*Primary Examiner* — Jennifer Robertson
*Assistant Examiner* — Elina Sohyun Jang
(74) *Attorney, Agent, or Firm* — Li & Cai Intellectual Property (USA) Office

(57) ABSTRACT

A wearable device and a method for performing a registration process in the wearable device are provided. The wearable device includes a light source, a light sensor and a microcontroller that performs the method. In the method, the light source is activated to emit a detection light and the light sensor senses a reflected light. A light intensity of the reflected light is calculated. Specifically, an upper limit and a lower limit are referred to for detecting whether the wearable device is properly worn by a person. For example, since the wearable device can be worn on the person's wrist, the registration value is used to detect whether the wearable device is away from the wrist.

16 Claims, 8 Drawing Sheets

WEARABLE DEVICE AND METHOD FOR PERFORMING REGISTRATION PROCESS IN THE WEARABLE DEVICE

CROSS-REFERENCE TO RELATED PATENT APPLICATION

This application is a continuation application of the U.S. patent application Ser. No. 17/030,546, filed on Sep. 24, 2020, and entitled "WEARABLE DEVICE AND METHOD FOR PERFORMING REGISTRATION PROCESS IN THE WEARABLE DEVICE". The entirety of each of the above patent applications is hereby incorporated by reference herein and made a part of this specification.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a wearable device, and more particularly to the wearable device that incorporates a registration value generated based on a light intensity measured in a method as the registration value for registering the wearable device.

BACKGROUND OF THE DISCLOSURE

With a growing number of people adopting a health-conscious lifestyle, a variety of portable health monitoring device are offered on the market for regularly monitoring the heath data of the people. The portable health monitoring device can be worn on a person's body, e.g., the person's wrist, and therefore the device can be used to sense health data of the person when worn around the person's wrist.

For example, the portable health monitoring device uses a light source to emit light to the skin of the person's wrist, and uses a light sensor to sense the reflected light from the skin of the wrist so as to collect the health data. The health data to be monitored by the portable health monitoring device can be a heart rate when the device is able to read the heartbeat waveforms.

The portable health monitoring device, e.g., a wrist-wearable device, should be properly worn on the person, such that the device can collect correct data and then obtain the correct analysis of the health data. Therefore, it is necessary for a portable device to be able to determine whether or not the portable device is properly worn on the person in order to make sure that the device can obtain the correct data.

However, it is difficult to determine whether or not a wearable device is properly worn on the person when only a G-sensor is used in the wearable device.

In a conventional technology, the wrist-wearable device uses the light emitted by its own light source to confirm whether the device is properly worn by detecting the brightness of light reflected from the wrist. However, the conventional wrist-wearable device cannot always obtain an accurate distance between the conventional wrist-wearable device and the person's wrist when only one factor, such as the brightness of the reflected light, is used for the determination.

SUMMARY OF THE DISCLOSURE

In response to the above-referenced technical inadequacies, the present disclosure provides a wearable device and a method for performing a registration process in the wearable device.

In an embodiment of the disclosure, the wearable device includes a light source that is configured to emit a detection light, a light sensor that is configured to sense the detection light reflected from an object, and a microcontroller electrically connected with the light source and the light sensor performs the method for performing a registration process in the wearable device.

In an aspect of the disclosure, in the method, the detection light is adjusted to cover different wavelength ranges. A light intensity is obtained based on the light sensed by the light sensor. A registered high threshold that serves as an upper limit and a registered low threshold that serves as a lower limit are referred to for detecting whether the wearable device is properly worn by a person based on the sensed light intensity The registered high threshold and the registered low threshold are stored in the memory.

In one aspect of the disclosure, the detection light includes different light rays corresponding to different wavelengths, and the registered high threshold or the registered low threshold is obtained when a specific light ray is emitted to the object. For example, the detection light is adjusted to emit at least a first light ray and a second light ray, and the first light ray is determined as the specific light ray when the first light ray causes a larger light intensity sensed by the light sensor than the second light ray.

In another aspect of the disclosure, the detection light includes different light rays corresponding to different wavelengths, and the registered high threshold or the registered low threshold is determined when a specific combination of light rays is emitted to the object. The detection light is adjusted to emit at least a first combination of light rays and a second combination of light rays, and the first combination of light rays is determined as the specific light ray when the first combination of light rays causes a larger light intensity sensed by light sensor than the second combination of light rays.

Still further, through the wearable device works normally if the sensed light intensity is between the registered high threshold and the registered low threshold; and a crucial function executed in the wearable device is terminated if the sensed light intensity is higher than the registered high threshold or is lower than the registered low threshold.

In the wearable device of the aspect, the light source can be a single pixel light source that is able to emit different frequencies of lights and different intensities of lights. Alternatively, the light source can be an arrayed light source that is able to emit multiple lights with different frequencies and intensities simultaneously.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The present disclosure will become more fully understood from the following detailed description and accompanying drawings.

DETAILED DESCRIPTION OF THE EXEMPLARY EMBODIMENTS

Figure 1:
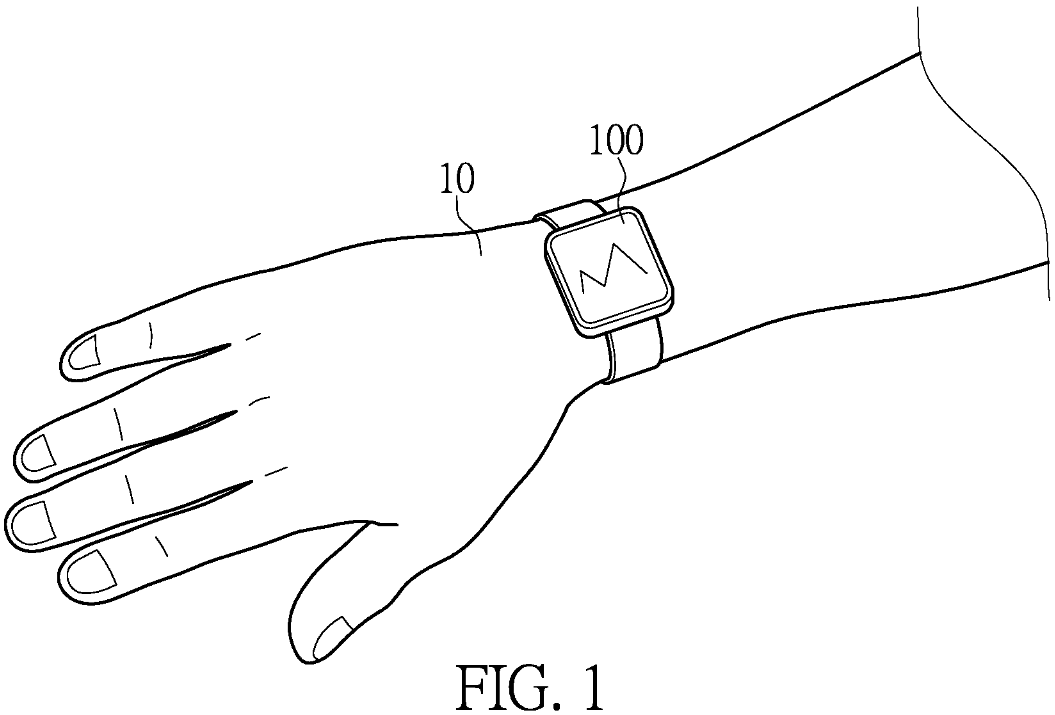
FIG. 1 is a schematic diagram that depicts a circumstance where a wearable device is worn on a person.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

The disclosure is related to a wearable device that is designed to be worn on a person's body, especially the wrist of the person, e.g., a wristband, a watch, or a sport bracelet. The wearable device may include sensors to sense some health data such as heart rate, breath, steps, etc. Therefore, through the wearable device worn on the person's wrist, the person can monitor his heart rate, observe sleeping status, record exercise data and so on. Furthermore, a powerful wearable device can also be used as a payment tool. For example, the wearable device can be equipped with an NFC (near-field communication) chip, an RFID (radio frequency identification) chip or the like that can be used to transfer payment information to another device for facilitating a financial transaction. In another example, the wearable device can also show a payment credential such as a barcode or a QR (quick response) code that allows a scanner to read the payment information for the further financial transaction.

In an exemplary example, reference is made to FIG. 1, which is a schematic diagram that depicts a circumstance that a wearable device 100 is worn on a person's wrist 10. For security considerations, before the financial transaction is performed, a monitoring sequence executed in the wearable device 100 is used to monitor whether or not the wearable device 100 is properly worn on the wrist 10. The transaction will be prohibited once the wearable device 10 is determined to be not properly worn by the person. One essential method to conduct the monitoring is to detect a distance between the wearable device 100 and the wrist 10.

In an aspect, the wearable device 100 is determined as in an off-wrist or off-body state if the distance between the wearable device 100 and the wrist 10 is greater than a registered threshold. Some crucial functions may be prohibited when the wearable device 100 is determined to be not properly worn by the person.

In another exemplary example, the wearable device is configured to collect the person's health data constantly. However, a data collection function of the wearable device 100 may be suspended when the wearable device 100 is determined as in the off-wrist or off-body state.

According to one of the embodiments, the wearable device 100 of the disclosure includes one or more light sources and a light sensor. The mentioned method of the disclosure can be adapted to many types of the light sources that are installed in the wearable device. For example, the light source can be a single pixel light source that is able to emit light with different wavelengths in turns; or the light source can be an arrayed-light source that is able to emit multiple lights with different wavelengths simultaneously, and wherein the lights with different wavelengths have different intensities or have the same intensity. In another embodiment, the light source can emit a light with widely wavelengths (e.g., white light). It should be noted that the implementation of the light source is not limited in the present disclosure, and may be modified by persons skilled in the art based on the practical requirements.

A distance-based off-wrist determination can be implemented by collaboration of the light source and the light sensor. In an aspect, an intensity (or brightness) of light sensed by the light sensor can be used to estimate a contacting state between the light source and an object reflecting the light according to an inverse square relationship. The intensity of the light sensed by the light sensor can be expressed by brightness. A brightness value can be measured based on a rate of the light energy being delivered to the light sensor and the light energy generated by the light source. Therefore, referring to the diagram shown in FIG. 1, an off-wrist or off-body determination can be based on the intensity of light sensed by the light sensor of the wearable device 100 from the light reflected by the skin surface of the wrist 10 of the person.

However, it can be understood that the different colors of skin have different reflectivity for a detection light and therefore result in an erroneous result when measuring the intensity of light in order to determine whether or not the wearable device is properly worn on the person. For example, a white skin, a dark skin and a tattooed skin will reflect different intensities of light since they have different reflectivity of light. Accordingly, a general purpose of a method for performing a registration process in the wearable device of the disclosure is to eliminate the erroneous determination for the different colors of skin.

The major aspect of the method performed in the wearable device requires a user who wears the wearable device to set up a registration value as a threshold proprietary to the user at an early stage when initializing the device. For example, the user shall properly wear the wearable device when the device is in an initialization process that also initiates a registration process, and the light source of the wearable device is activated to emit a detection light with a specific intensity or a specific frequency, or any combination of various intensities and frequencies. It should be noted that the frequency of a frequency-variable light source can be controlled by a control circuitry so as to modulate the frequency or color of the emitting light; furthermore, a power of the light source can also be controlled for emitting the light with a specific intensity. Afterwards, a registration value is used to record an intensity value of the light reflected from the skin of the user in the registration process. The registration value can be used as a reference to determine whether or not the person properly wears the wearable device.

Figure 2:
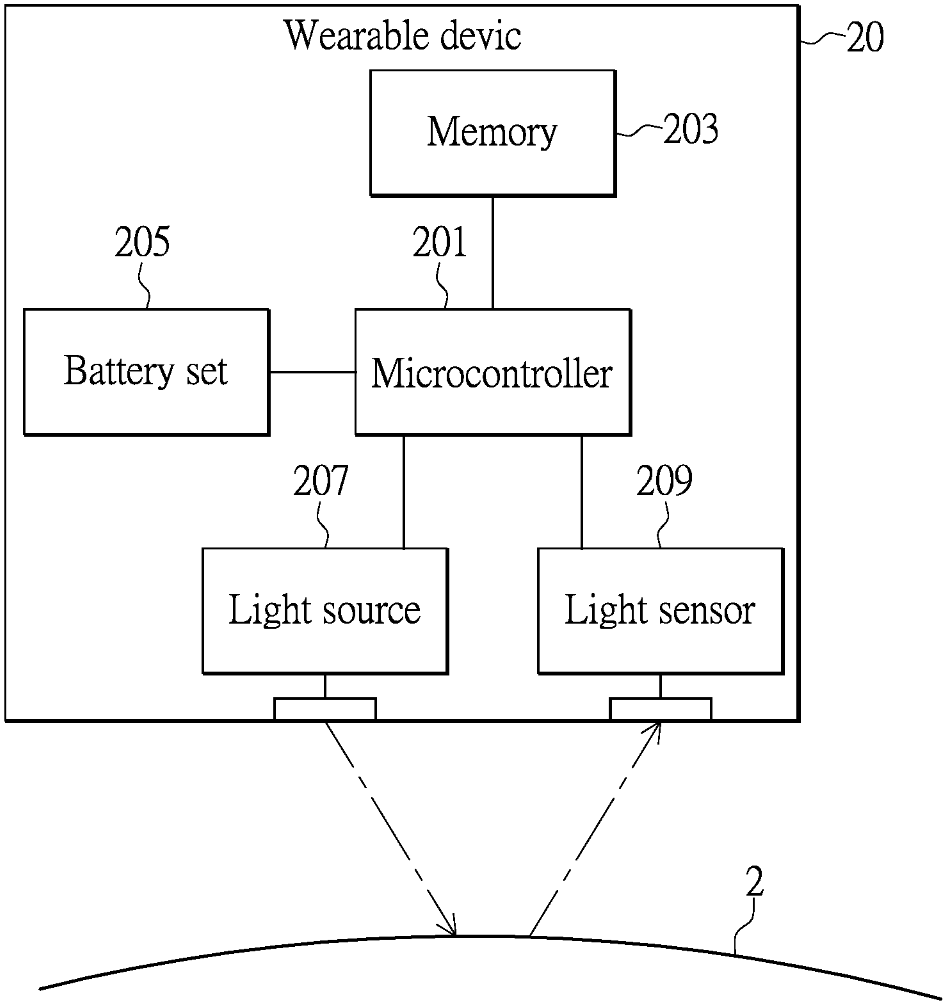
FIG. 2 depicts a circuit block diagram of the wearable device according to one embodiment of the disclosure.

FIG. 2 depicts a circuit block diagram of the wearable device according to one embodiment of the disclosure. In FIG. 2, a wearable device 20 can be a wrist-worn device that is not used to limit the scope of the present disclosure, and the wearable device 20 can also be various other devices that can be worn on a person's body in other embodiments.

The wearable device 20 includes a microcontroller 201 that can be implemented by any type of circuitry in the device for operating the wearable device 20. Main circuit components of the wearable device 20 include a light source 207, a light sensor 209, a memory 203, a battery set 205 and the microcontroller 201 that is electrically connected with the components. The light source 207 (one or more light sources) can be a light-emitted diode (LED) or a laser diode (LD) that is configured to emit a detection light through a window. The light sensor 209 is used to sense the detection light reflected from an object 2 through another window. The memory 203 is used to store the registration value which records the intensity of the light reflected from the skin of the user in the registration process. The microcontroller 201 performs the method for performing a registration process in the wearable device 20.

In the wearable device, the detection light emitted by the light source can be adjusted to cover different wavelength ranges, and the registration value is determined based on the light intensity sensed when the detection light is emitted in a specific wavelength range.

In one embodiment, the detection light includes different light rays corresponding to different wavelengths. In which, at least two of the different light rays emit in different intensities. The registration value can be obtained when a specific light ray is emitted to the object, or can be determined when a specific combination of light rays is emitted to the object.

More specifically, the detection light can be adjusted to emit at least a first light ray and a second light ray, and the first light ray is determined as the specific light ray when the first light ray causes a larger light intensity sensed by the light sensor than the second light ray.

Figure 3:
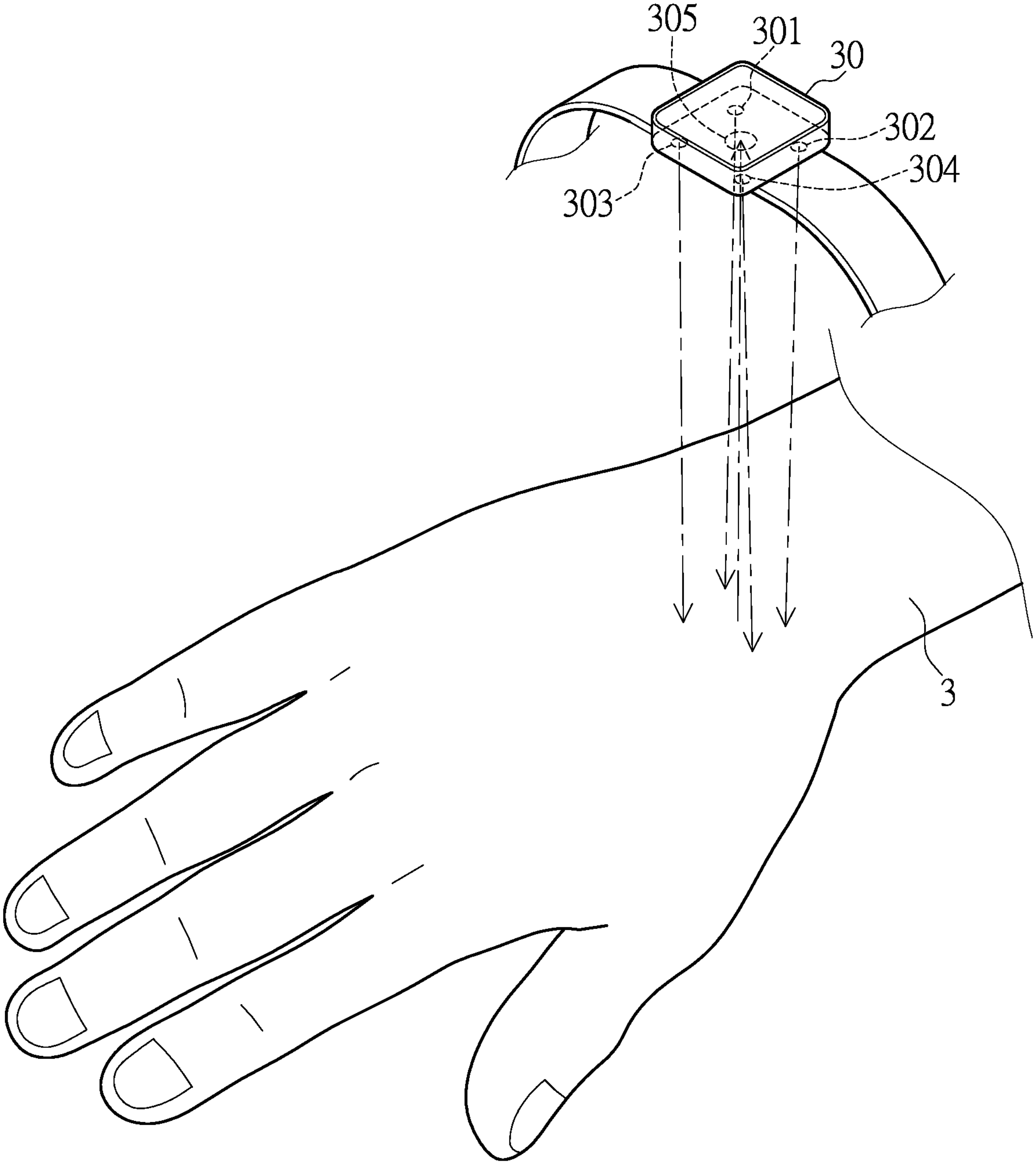
FIG. 3 is a schematic diagram that depicts a wearable device using multiple light sources to form a registration value according to one embodiment of the disclosure.

Reference is next made to FIG. 3, which is a schematic diagram depicting a wearable device using multiple light sources. A wearable device 30 as shown in the diagram includes multiple light sources 301, 302, 303 and 304 at the side toward an object 3, and a light sensor 305 at the same side of the device.

The multiple light sources 301, 302, 303 and 304 can emit the detection lights with different intensities or different frequencies such that the light sensor 305 can sense the lights reflected by the object 3 with various intensities and various frequencies. Therefore, the registration value stored in the memory of the wearable device 30 may select one of the intensities of the reflected lights as the threshold to determine whether the wearable device is properly worn by the user. It should be noted that, the intensities sensed by the light sensor 305 can be referred to set up one threshold or multiple thresholds including an upper threshold and a lower threshold.

The disclosure provides a distance-based method for off-wrist or off-body determination that allows the wearable device itself to determine whether or not the device is properly worn on the person. For example, when the wearable device exemplarily shown on FIGS. 1 to 3 is worn on the wrist, a distance between the device and the wrist should be small. Therefore, the distance between the device and wrist can be used as a reference to conduct the off-wrist or off-body determination. The light source and the light sensor equipped in the wearable device forms an optical sensing system that can be used to estimate the distance based on the light intensity and to conduct the determination. As the different colors of skin will produce different results in the optical sensing system, the method provides every user to have his proprietary reference for the off-wrist or off-body determination. Therefore, the method for performing a registration process in the wearable device of the disclosure can effectively eliminate erroneous determination.

Figure 4:
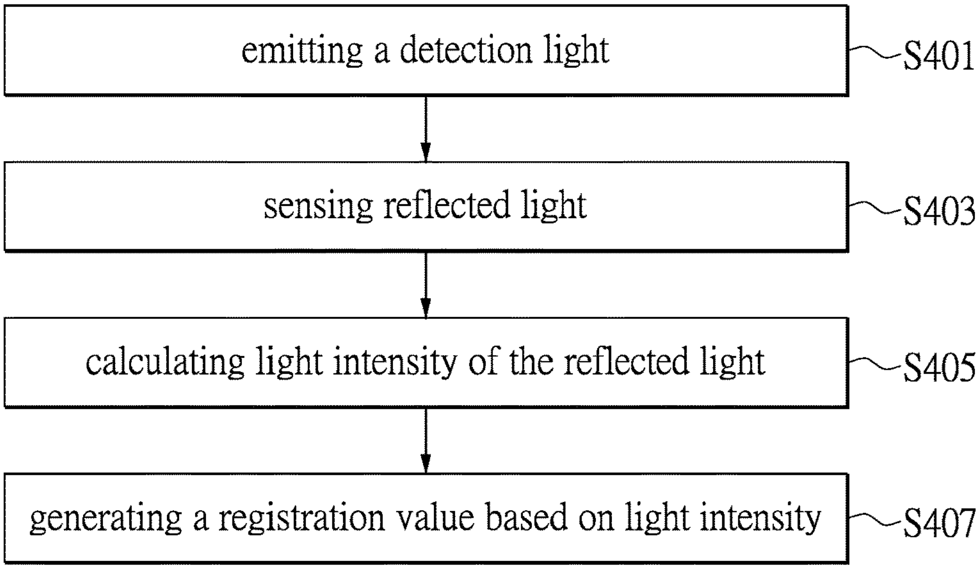
FIG. 4 is a flow chart that describes a method for performing a registration process in the wearable device in an initialization process according to one embodiment of the disclosure.

FIG. 4 is a flow chart that describes the method for performing a registration process in the wearable device in an initialization process according to one embodiment of the disclosure.

In the initialization process of the wearable device, a user who wears the wearable device is required to manipulate the wearable device to initiate a registration process. For example, a message shown on the wearable device guides the user to initiate the registration process. In the meantime, a light source (one or more light sources) of the wearable device is activated to emit a detection light toward the skin of the user (step S401). A light sensor of the wearable device then senses the reflected light from the skin of the user (step S403). A light intensity of the reflected light can be obtained (step S405). It should be noted that, the light intensity can be expressed as a brightness value that may be varied with respect to different colors of skin. A registration value is then generated based on the light intensity (step S407) and then stored to the memory of the wearable device. When the registration value is generated, another message may be shown on the wearable device for notifying the user to confirm the registration process is done.

It is appreciated that the registration value stored in the wearable device acts as a threshold to detect whether the wearable device is properly worn by the user, and it is believed that the registration value generated by the method of the disclosure forms a more accurate threshold for people with different colors of skin. The method also forms an appropriate threshold for people having tattoo on the skin where the wearable device contacts.

Figure 5:
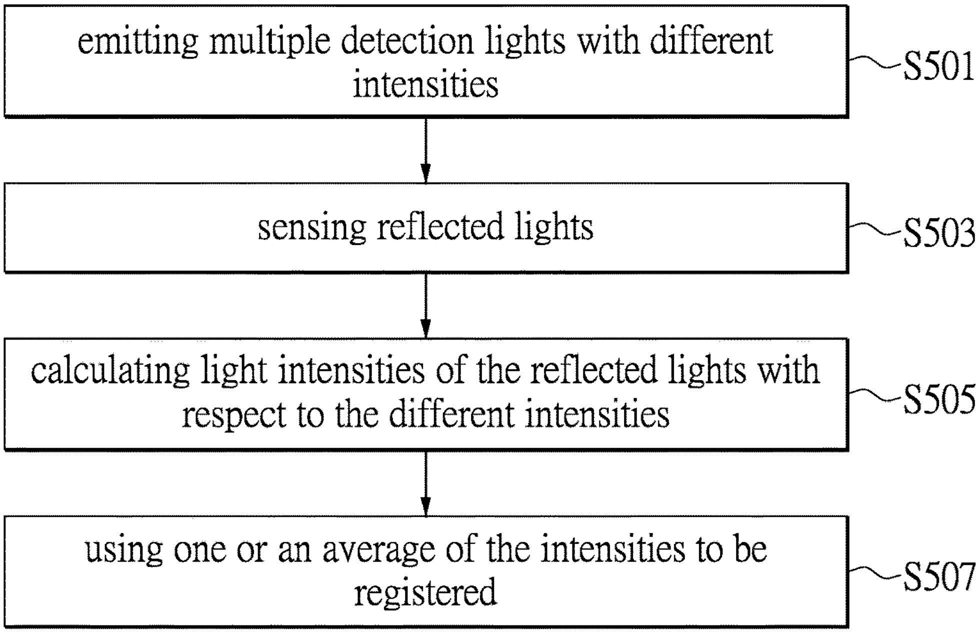
FIG. 5 is another flow chart describing the method for performing a registration process in the wearable device according to another embodiment of the disclosure.

FIG. 5 is another flow chart describing the method for performing a registration process in the wearable device according to another embodiment of the disclosure.

The light source of the wearable device may emit multiple detection lights with different intensities toward the skin of the user (step S501). The light sensor then senses the reflected lights with different intensities (step S503). Therefore, multiple light intensities with respect to the reflected lights can be calculated in the wearable device (step S505). The user can choose one of the light intensities to be the threshold (step S507). Alternatively, a computer sequence executed in the wearable device can automatically select one of the light intensities of the reflected lights to be the threshold, in which some unreasonable values may be excluded when selecting the intensity value. Further, if multiple intensities measured from the reflected lights as excluding some unreasonable values are obtained by the computer sequence, a maximum, a minimum or an average of the intensities can also be calculated as the registration value to be registered in the wearable device. A related registration value can be formed as the threshold for determining if the wearable device is away from the wrist or a specific portion of the body.

Figure 6:
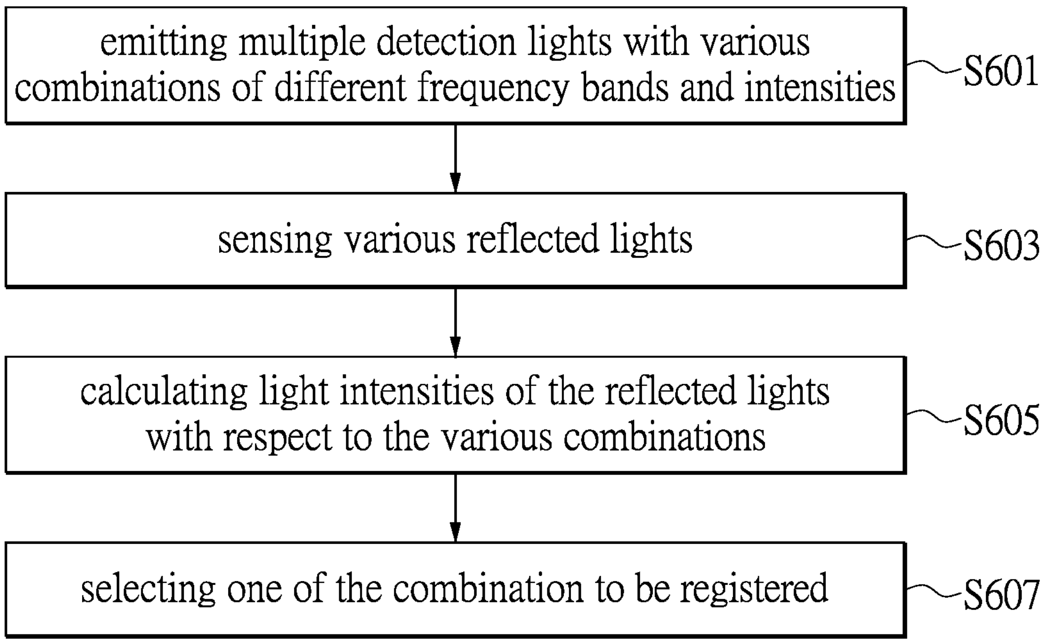
FIG. 6 is one further flow chart describing the method performing a registration process in the wearable device according to one further embodiment of the disclosure.

Next, reference is made to FIG. 6, which shows a flow chart describing the method for performing a registration process in the wearable device in another embodiment of the disclosure.

When the wearable device is in the registration process, the light source can be activated to emit multiple detection lights with various combinations of different frequencies and intensities (step S601). For example, a control circuitry of the light source(s) of the wearable device is configured to sequentially control powers and/or frequencies of the light source(s) so as to emit various detection lights with various intensities and/or frequencies. Therefore, the light sensor of the wearable device can sense various lights reflected by the object receiving the detection lights (step S603). In the microcontroller of the wearable device, the computer sequence executed therein calculates a series of light intensities of the reflected lights with respect to the various combinations of the frequencies and the intensities (step S605). Afterwards, one of the combinations of the intensities and frequencies forms a registration value that is registered in the registration process and stored in the memory of the wearable device (step S607). The related registration value forms a threshold to determine whether or not the wearable device is properly worn on the person initiating the registration process in a normal operation.

In an exemplary example, the detection light can be adjusted to emit at least a first combination of light rays and a second combination of light rays. Specifically, the first combination of light rays is determined as the specific light ray when the first combination of light rays causes a larger light intensity sensed by light sensor than the second combination of light rays.

Figure 7:
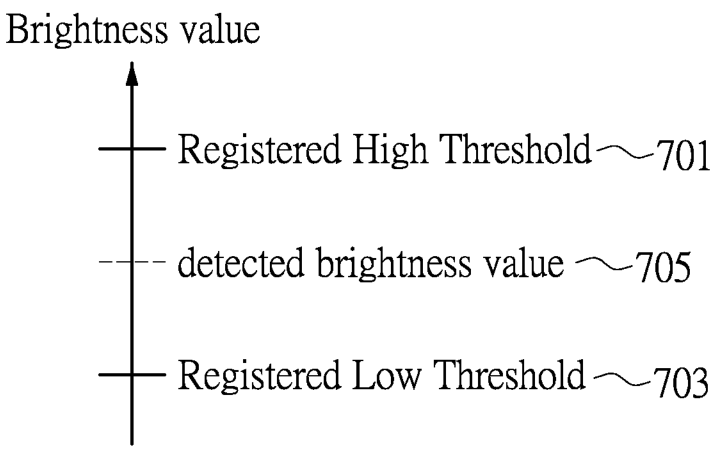
FIG. 7 is a schematic diagram depicting the thresholds to be registered for the wearable device according to one embodiment of the disclosure.

FIG. 7 shows a schematic diagram that depicts the thresholds to be registered for the wearable device according to one further embodiment of the disclosure.

In one of the embodiments of the disclosure, when an intensity value or a combination of intensity and frequency is registered as a registration value for the wearable device, the registration value acts as a threshold to detect whether the wearable device is properly worn by a person. In one aspect of the disclosure, the threshold may not be an exact number, but a range of thresholds.

For example, in FIG. 7, an axis of brightness value is used to mark the brightness value that indicates an intensity value of light. The diagram shows a registered high threshold 701, a registered low threshold 703 and a detected brightness value 705 that are marked on the axis of brightness value. The registration value generated in the registration process of the wearable device allows the computer sequence to deduce the registered high threshold 701 as an upper limit and the registered low threshold 703 as a lower limit that are referred to so as to perform the off-wrist or off-body determination based on condition of the person's skin.

In an exemplary example, when the wearable device is in operation, the detected brightness value 705 is generated and compared with the registered high threshold 701 and the registered low threshold 703. The wearable device can work normally if the detected brightness value 705 is between the registered high threshold 701 and the registered low threshold 703; otherwise, a crucial function executed in the wearable device may be terminated.

Based on the above-mentioned mechanism that the wearable device will be registered with a registration value that is proprietary to the user who wears the wearable device, the monitoring sequence executed in the microcontroller of the wearable device can constantly monitor the state of the wearable device. For example, the wearable device is not allowed to perform a function if the wearable device is determined to be away from the wrist.

Figure 8:
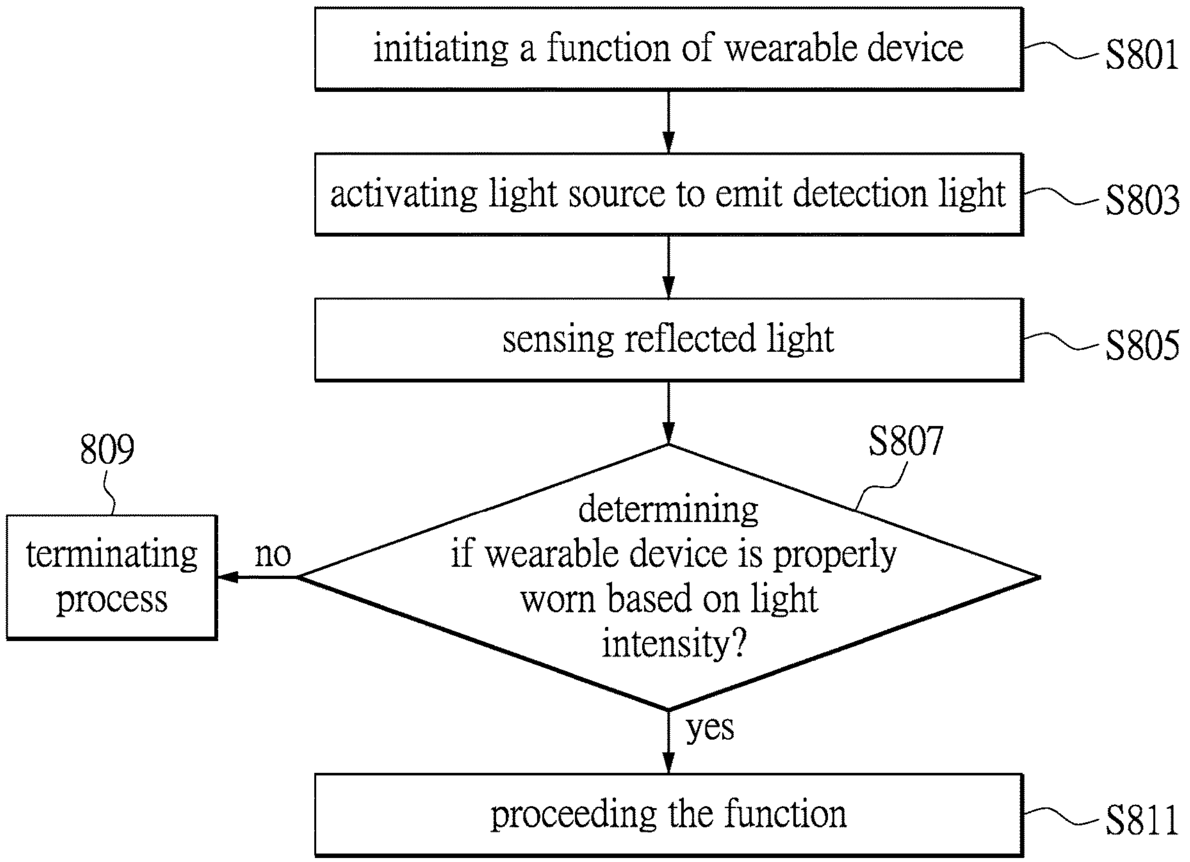
FIG. 8 is a flow chart describing a process introducing the registration value performed by the wearable device according to one embodiment of the disclosure.

FIG. 8 is a flow chart describing a process introducing the registration value performed by the wearable device according to one embodiment of the disclosure.

When a function of wearable device is initiated (step S801), the monitoring sequence executed in the wearable device generally activates a light source to emit a detection light (step S803), and a light sensor is activated to sense a reflected light (step S805). The intensity of the reflected light can be measured and used to compare with the threshold registered in the wearable device for determining if the wearable device is properly worn on a user based on the light intensity (step S807). According to the embodiments of the disclosure, the function initiated in the wearable device can be one of the crucial functions that require safety such as an action of payment, a process for collecting health data, and initiating a security procedure.

If the wearable device is determined properly worn on the user, the function will be proceeded (step S811). For example, the function can be a payment process performed by the wearable device. When the payment process is initiated, the monitoring sequence executed by the microcontroller of the wearable device also initiates an off-wrist determination process. Once the monitoring sequence confirms that the wearable device is properly worn on the user, the microcontroller makes the payment process to proceed or also allow continual payments after user authentication.

Otherwise, when the wearable device is determined not properly worn on the user, such as in step S809, the process such as the function executed in the wearable will be terminated. In an example, the monitoring sequence constantly performs the off-wrist determination process, and a message shown on the wearable device notifies the user to wear the device properly if the process is terminated. Afterwards, the user may be required to be authenticated again for re-initiating the function.

Furthermore, the method for performing a registration process in the wearable device is provided for the wearable device to be adapted to various skin colors, or even skins with various types of tattoos, as the method is able to generate the registration value forming the threshold proprietary for people. The method meets the security requirements of the wearable device when the wearable device is configured to perform the crucial functions that require the person to properly wear the wearable device.

The various skin types can be defined as Fitzpatrick skin types. For example, skin of an ivory color is defined as Fitzpatrick skin type I; fair or pale skin is defined as Fitzpatrick skin type II; fair to beige with golden undertones skin is defined as Fitzpatrick skin type III; olive or light brown skin is defined as Fitzpatrick skin type IV; dark brown skin is defined as Fitzpatrick skin type V; and deeply pigmented dark brown to darkest brown skin is defined as Fitzpatrick skin type VI.

Figure 9A:
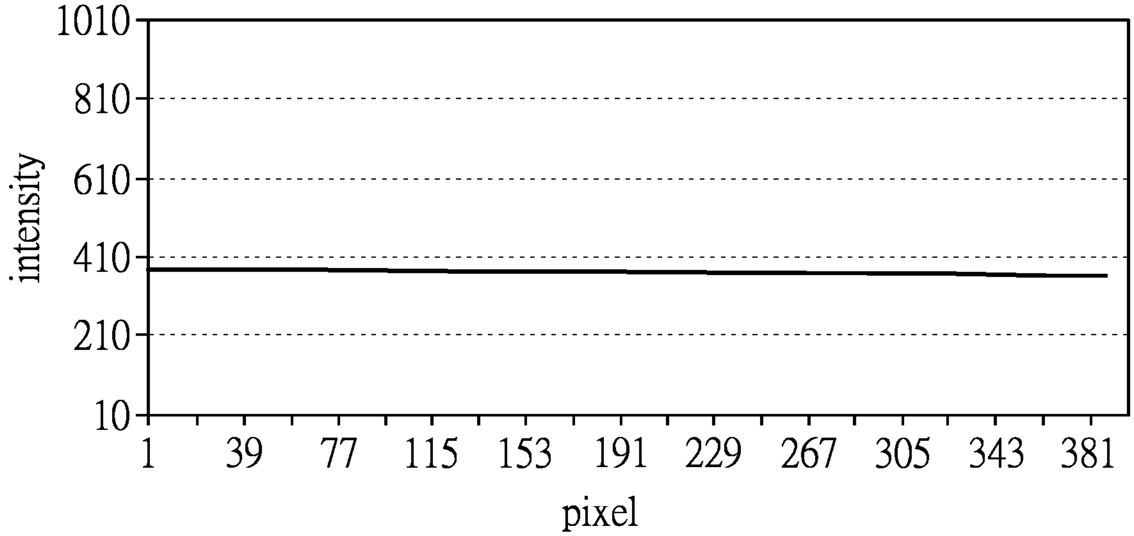
FIG. 9A and FIG. 9B show the light intensities obtained from different detection lights emitted on a Fitzpatrick skin type III skin.
Figure 9B:
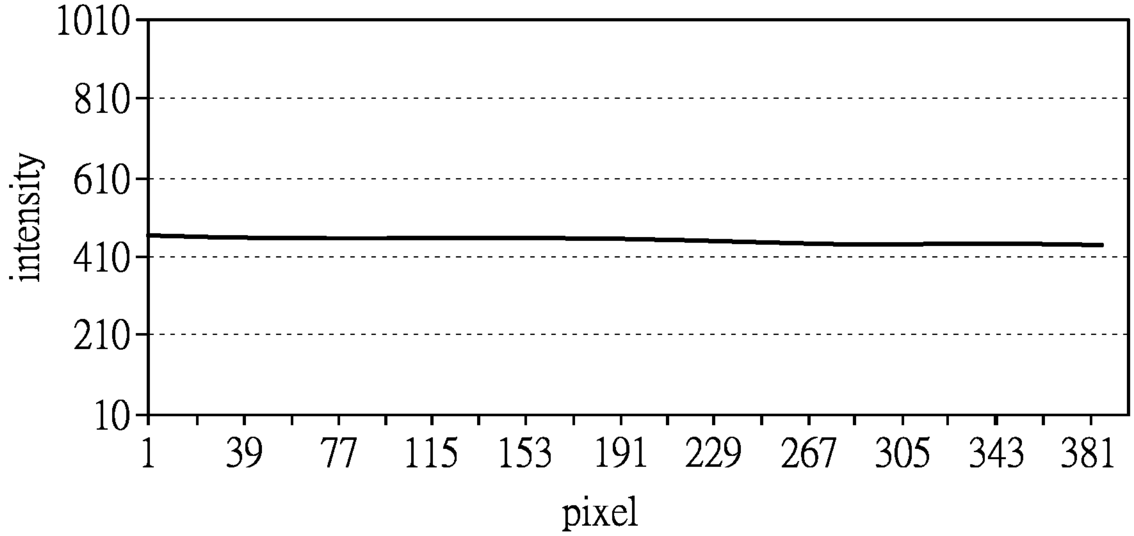

FIG. 9A and FIG. 9B exemplarily show that the different light intensities sensed by the light sensor from two different detection lights (i.e., first light source of FIG. 9A and second light source of FIG. 9B) emitted on Fitzpatrick skin type III skin.

Figure 10A:
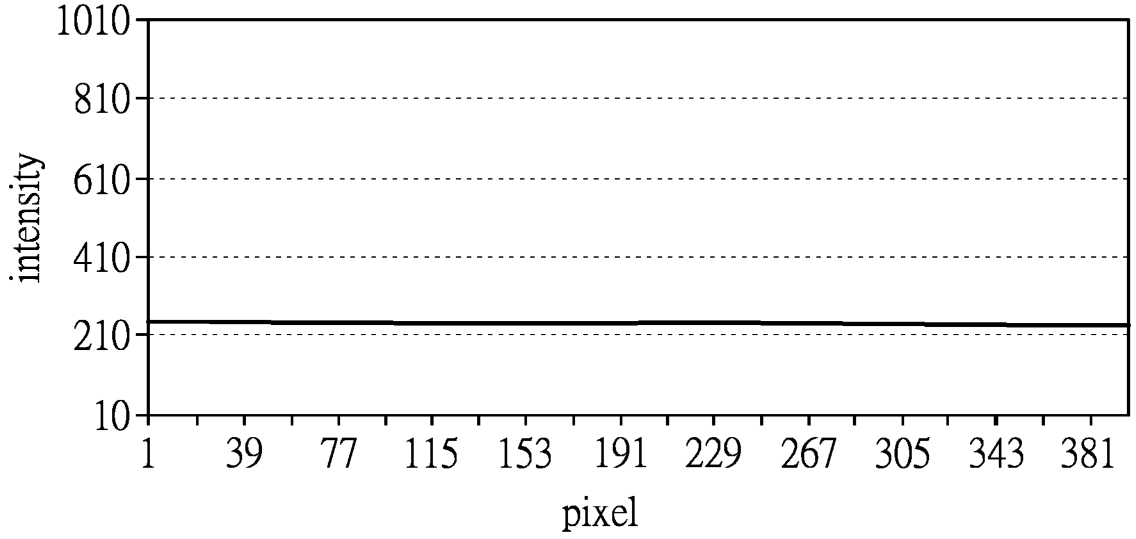
FIG. 10A and FIG. 10B show the light intensities obtained from different detection lights emitted on a Fitzpatrick skin type IV skin.
Figure 10B:
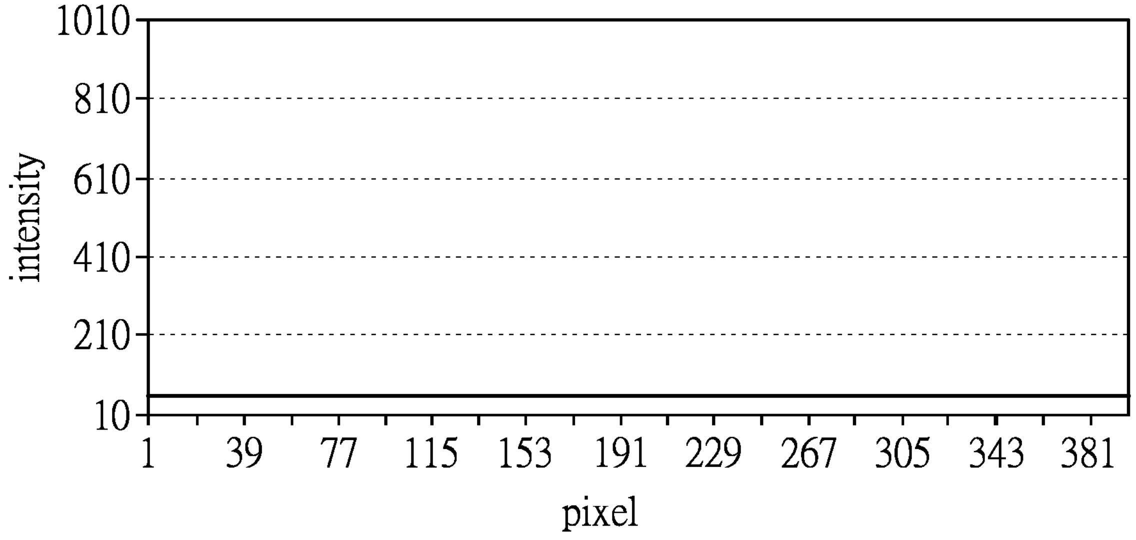

FIG. 10A and FIG. 10B exemplarily show the different light intensities obtained from two different detection lights (i.e., first light source of FIG. 10A and second light source of FIG. 10B) emitted on Fitzpatrick skin type IV skin.

In conclusion, according to the above embodiments of the disclosure, the method for performing a registration process in the wearable device is provided for registering a proprietary threshold for the user and allows the wearable device to accurately determine whether or not the user properly wears the wearable device. Specifically, the threshold is produced based on the condition of skin of the user, and when the wearable device is in an initialization process, the light intensity registered as the threshold is sensed by the light sensor of the wearable device. The method performed by the wearable device can effectively eliminate the erroneous determination for various conditions of skin. Further, the wearable device performing the registration process in the method can ensure that the device safely performs the functions, since the monitoring sequence executed in the device constantly detects whether or not the wearable device is properly worn by the user before the functions are performed.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A method for performing a registration process in a wearable device, comprising:

activating a light source of the wearable device to emit a detection light;

obtaining a light intensity sensed by a light sensor that is configured to sense the detection light reflected by or passing through an object, wherein the detection light is adjusted to emit at least a first combination of light rays and a second combination of light rays, and the first combination of light rays is determined as a specific light ray to be emitted to the object when the first combination of light rays causes a larger light intensity sensed by the light sensor than the second combination of light rays, wherein the object is skin of a specific portion of body of any one of persons having different skin conditions;

in response to the light intensity, generating a registered high threshold and a registered low threshold proprietary to a person who wears the wearable device based on the person's skin condition, wherein the registered high threshold serves as an upper limit and the registered low threshold serves as a lower limit that are referred to for detecting whether or not the wearable device is worn by the person for able to perform a function at least relating to security based on the light intensity;

wherein, when the wearable device is in operation, a sensed light intensity is generated and compared with both the registered high threshold and the registered low threshold so as to determine if the function at least relating to security executed in the wearable device is terminated.

2. The method according to claim 1, wherein the detection light is adjusted to cover different wavelength ranges, and the registered high threshold or the registered low threshold is determined based on the light intensity sensed when the detection light is emitted in a specific wavelength range.

3. The method according to claim 2, wherein the detection light includes different light rays corresponding to different wavelengths, and the registered high threshold or the registered low threshold is obtained when the specific light ray is emitted to the object.

4. The method according to claim 2, wherein the detection light includes different light rays corresponding to different wavelengths, and the registered high threshold or the registered low threshold is determined when a specific combination of light rays is emitted to the object.

5. The method according to claim 2, wherein the detection light includes different light rays corresponding to different wavelengths, and at least two of the different light rays emit in different intensities.

6. The method according to claim 1, wherein the wearable device is in operation if the sensed light intensity is between the registered high threshold and the registered low threshold; and the function at least relating to security executed in the wearable device is terminated if the sensed light intensity is higher than the registered high threshold or is lower than the registered low threshold.

7. The method according to claim 1, wherein the wearable device is configured to be worn on a wrist of the person, and the registered high threshold and the registered low threshold are used to detect whether the wearable device is away from the wrist, and the wearable device is not allowed to perform the function at least relating to security if the wearable device is determined to be away from the wrist.

8. The method according to claim 7, wherein the wearable device terminates the current operation if the wearable device is determined to be away from the wrist.

9. A wearable device, comprising:

a light source configured to emit a detection light;

a light sensor configured to sense the detection light reflected from an object;

a memory; and a microcontroller electrically connected with the light source, the light sensor and the memory, and performing a method for performing a registration process in the wearable device, the method including:

activating the light source to emit the detection light, wherein the detection light is adjusted to emit at least a first combination of light rays and a second combination of light rays, and the first combination of light rays is determined as a specific light ray to be emitted to the object when the first combination of light rays causes a larger light intensity sensed by the light sensor than the second combination of light rays, wherein the object is skin of a specific portion of body of any one of persons having different skin conditions;

obtaining a light intensity sensed by the light sensor;

in response to the light intensity, generating a registered high threshold and a registered low threshold proprietary to a person who wears the wearable device based on the person's skin condition, wherein the registered high threshold serves as an upper limit and the registered low threshold serve s as a lower limit that are referred to for detecting whether the wearable device is worn by the person for able to perform a function at least relating to security based on the light intensity; and storing the registered high threshold and the registered low threshold in the memory;

wherein, when the wearable device is in operation, a sensed light intensity is generated and compared with both the registered high threshold and the registered low threshold so as to determine if the function at least relating to security executed in the wearable device is terminated.

10. The wearable device according to claim 9, wherein the detection light is adjusted to cover different wavelength ranges, and the registered high threshold or the registered low threshold is determined based on the light intensity sensed when the detection light is emitted in a specific wavelength range.

11. The wearable device according to claim 10, wherein the detection light includes different light rays corresponding to different wavelengths, and the registered high threshold or the registered low threshold is obtained when a specific light ray is emitted to the object.

12. The wearable device according to claim 10, wherein the detection light includes different light rays corresponding to different wavelengths, and the registered high threshold or the registered low threshold is determined when a specific combination of light rays is emitted to the object.

13. The wearable device according to claim 9, wherein the wearable device is in operation if the sensed light intensity is between the registered high threshold and the registered low threshold; and the function at least relating to security executed in the wearable device is terminated if the sensed light intensity is higher than the registered high threshold or is lower than the registered low threshold.

14. The wearable device according to claim 9, wherein the wearable device is configured to be worn on a wrist of the person and the registered high threshold and the registered low threshold are used to detect whether the wearable device is away from the wrist; and the wearable device is not allowed to perform the function at least relating to security if the wearable device is determined to be away from the wrist.

15. The wearable device according to claim 9, wherein the light source is a single pixel light source that is able to emit different frequencies of lights and different intensities of lights.

16. The wearable device according to claim 9, wherein the light source is an arrayed light source that is able to emit multiple lights with different frequencies and intensities simultaneously.

* * * * *